(12) United States Patent
Dell'Oca

(10) Patent No.: US 10,524,816 B2
(45) Date of Patent: Jan. 7, 2020

(54) TUNNEL TOOL FOR SOFT TISSUE

(75) Inventor: Alberto A. Fernandez Dell'Oca, Montevideo (UY)

(73) Assignee: DePuy Synthes Products, Inc., Raynham, MA (US)

( * ) Notice: Subject to any disclaimer, the term of this patent is extended or adjusted under 35 U.S.C. 154(b) by 1925 days.

(21) Appl. No.: 12/515,817

(22) PCT Filed: Jan. 31, 2008

(86) PCT No.: PCT/US2008/052557
§ 371 (c)(1),
(2), (4) Date: May 21, 2009

(87) PCT Pub. No.: WO2008/097789
PCT Pub. Date: Aug. 14, 2008

(65) Prior Publication Data
US 2010/0023042 A1    Jan. 28, 2010

Related U.S. Application Data

(60) Provisional application No. 60/899,041, filed on Feb. 2, 2007.

(51) Int. Cl.
*A61B 17/32* (2006.01)
*A61B 90/00* (2016.01)
*A61B 17/34* (2006.01)

(52) U.S. Cl.
CPC .. *A61B 17/320016* (2013.01); *A61B 17/3494* (2013.01); *A61B 2017/320044* (2013.01);
(Continued)

(58) Field of Classification Search
CPC .. A61B 17/32002; A61B 2017/320052; A61B 2017/320056; A61B 17/34;
(Continued)

(56) References Cited

U.S. PATENT DOCUMENTS 2,623,521 A * 12/1952 Shaw ................. 604/170.02
3,809,095 A *  5/1974 Cimber ............... A61M 25/06
                                              604/157

(Continued)

FOREIGN PATENT DOCUMENTS

DE      19707374      8/1998
WO      96/10361      4/1996
(Continued)

*Primary Examiner* — Darwin P Erezo
*Assistant Examiner* — Erin L Colello
(74) *Attorney, Agent, or Firm* — Fay Kaplun & Marcin, LLP

(57) ABSTRACT

A device (100) for creating a tunnel through soft tissue, comprises an elongated insertion member including a lumen extending therethrough to a distal opening, the elongated insertion member being sized to be inserted into the body via an opening of no more than 35 mm diameter and a tunneling member (108) received in the lumen for movement between an insertion configuration in which a tissue penetrating distal tip is received within the lumen and a tunneling configuration in which the distal tip extends distally from the distal opening by a desired distance in combination with a handle (104) coupled to a proximal end of the insertion member, the handle remaining outside the body and including a first actuator (106) for moving the tunneling member between the insertion and tunneling configurations.

17 Claims, 5 Drawing Sheets

(52) U.S. Cl.
CPC ............. *A61B 2017/320056* (2013.01); *A61B 2090/034* (2016.02)

(58) Field of Classification Search
CPC ............ A61B 17/3417; A61B 17/3494; A61B 17/3496; A61B 19/30; A61B 2019/304; A61B 17/32053; A61B 17/3472; A61B 2017/320044; A61B 18/1487; A61B 90/03; A61B 2090/033; A61B 2090/034; A61B 17/320016; A61B 2017/2925; A61B 2017/00336
USPC ........ 606/167, 190, 170, 184, 181, 182, 185, 606/79, 80; 600/564, 567
See application file for complete search history.

(56) References Cited

U.S. PATENT DOCUMENTS

| | | | | |
|---|---|---|---|---|
| 4,570,632 | A * | 2/1986 | Woods | 606/166 |
| 4,625,717 | A * | 12/1986 | Covitz | A61B 17/8861 606/103 |
| 4,828,547 | A * | 5/1989 | Sahi et al. | 604/110 |
| 4,962,770 | A * | 10/1990 | Agee | A61B 17/32003 128/898 |
| 5,002,546 | A * | 3/1991 | Romano | A61B 17/1628 408/127 |
| 5,104,382 | A * | 4/1992 | Brinkerhoff | A61B 17/3496 604/164.12 |
| 5,395,374 | A * | 3/1995 | Miller et al. | 606/74 |
| 5,406,940 | A * | 4/1995 | Melzer et al. | 600/106 |
| 5,483,952 | A * | 1/1996 | Aranyi | 600/131 |
| 5,511,556 | A * | 4/1996 | DeSantis | 600/567 |
| 5,515,861 | A * | 5/1996 | Smith | 600/567 |
| 5,529,580 | A * | 6/1996 | Kusunoki et al. | 606/170 |
| 5,569,160 | A * | 10/1996 | Sauer et al. | 600/114 |
| 5,611,352 | A * | 3/1997 | Kobren et al. | 600/564 |
| 5,620,456 | A * | 4/1997 | Sauer et al. | 606/185 |
| 5,669,885 | A * | 9/1997 | Smith | 606/184 |
| 5,676,156 | A * | 10/1997 | Yoon | 600/567 |
| 5,690,664 | A * | 11/1997 | Sauer et al. | 606/185 |
| 5,851,209 | A * | 12/1998 | Kummer | A61B 17/14 606/103 |
| 5,911,701 | A * | 6/1999 | Miller et al. | 604/22 |
| 5,911,729 | A * | 6/1999 | Shikhman et al. | 606/181 |
| 5,989,210 | A * | 11/1999 | Morris et al. | 604/22 |
| 6,224,570 | B1 * | 5/2001 | Le et al. | 604/165.02 |
| 6,814,734 | B2 * | 11/2004 | Chappuis et al. | 606/80 |
| 7,555,343 | B2 * | 6/2009 | Bleich | 607/43 |
| 7,578,819 | B2 * | 8/2009 | Bleich et al. | 606/53 |
| 7,691,052 | B2 * | 4/2010 | Gellman et al. | 600/30 |
| 7,815,642 | B2 * | 10/2010 | Miller | 606/79 |
| 7,857,813 | B2 * | 12/2010 | Schmitz et al. | 606/79 |
| 7,887,538 | B2 * | 2/2011 | Bleich et al. | 606/79 |
| 2001/0020139 | A1 | 9/2001 | Milliman et al. | |
| 2003/0069595 | A1 * | 4/2003 | Phung et al. | 606/184 |
| 2005/0090706 | A1 * | 4/2005 | Gellman et al. | 600/29 |
| 2005/0256452 | A1 | 11/2005 | DeMarchi et al. | |
| 2006/0004323 | A1 | 1/2006 | Chang et al. | |
| 2006/0064101 | A1 * | 3/2006 | Arramon | 606/82 |
| 2007/0083100 | A1 * | 4/2007 | Schulz-Stubner | 600/407 |

FOREIGN PATENT DOCUMENTS

| | | |
|---|---|---|
| WO | 2004/069498 | 8/2004 |
| WO | 2006/017507 | 2/2006 |

* cited by examiner though the tunneling element $108$ has been described as being

TUNNEL TOOL FOR SOFT TISSUE

The present application is a 371 application of PCT application Serial No. PCT/US2008/052557 filed on Jan. 31, 2008; which claims the benefit of U.S. Provisional Application Ser. No. 60/899,041 filed on Feb. 2, 2007. The disclosure of the above patent(s)/application(s) is incorporated herein by reference.

BACKGROUND OF THE INVENTION

The present invention relates to orthopedics, and more particularly to a device able for dissecting soft tissues surrounding bone to create space for the minimally invasive insertion of an implant adjacent to the bone.

Existing instruments to perform this task include blunt or sharp long rasps that require the application of large pushing forces to create a tunnel through the dense soft tissues surrounding around a bone. The large forces required reduce the users' control over the tips of these instruments increasing the risk of soft tissue and neurovascular damage. Moreover the insertion of existing instruments requires significant spreading of the incision adding to tissue trauma and making it difficult to work in more restricted areas.

SUMMARY OF THE INVENTION

It is an object of the present invention to provide a tool that creates a tunnel adjacent to a bone, via a small incision sized similarly to those employed in minimally invasive osteosynthesis.

It is a further object of the present invention to provide a device facilitating the creation of a tunnel while minimizing the risk of neurovascular and soft tissue damage.

The present invention is directed to a device for creating a tunnel through soft tissue, comprising an elongated insertion member including a lumen extending therethrough to a distal opening, the elongated insertion member being sized to be inserted into the body via an opening of no more than 35 mm diameter and a tunneling member received in the lumen for movement between an insertion configuration in which a tissue penetrating distal tip is received within the lumen and a tunneling configuration in which the distal tip extends distally from the distal opening by a desired distance in combination with a handle coupled to a proximal end of the insertion member, the handle remaining outside the body and including a first actuator for moving the tunneling member between the insertion and tunneling configurations.

First and second embodiments of the tunnel tool differ in two aspects—the shape of the tip of the hollow body of the tool and the flexibility of the plunger. The tip of the first embodiment has an almost constant radius and is used to tunnel along the bones in order to allow the insertion of a plate-like osteosynthetic device under the muscles, close to bone; the tip of the second embodiment of the present invention has a sharp bend at its frontal end and is used to tunnel around the bone in order to permit a cable or wire to be slid around the bone. Moreover, the plunger of the first embodiment is preferably rigid, while in the second embodiment the plunger is flexible.

DETAILED DESCRIPTION

The present invention, which may be further understood with reference to the following description and the appended drawings, relates to devices for treating fractures and, in particular, to devices for minimally invasive tunneling of soft tissue to create a space for the insertion of an implant adjacent to a bone.

Figure 1:
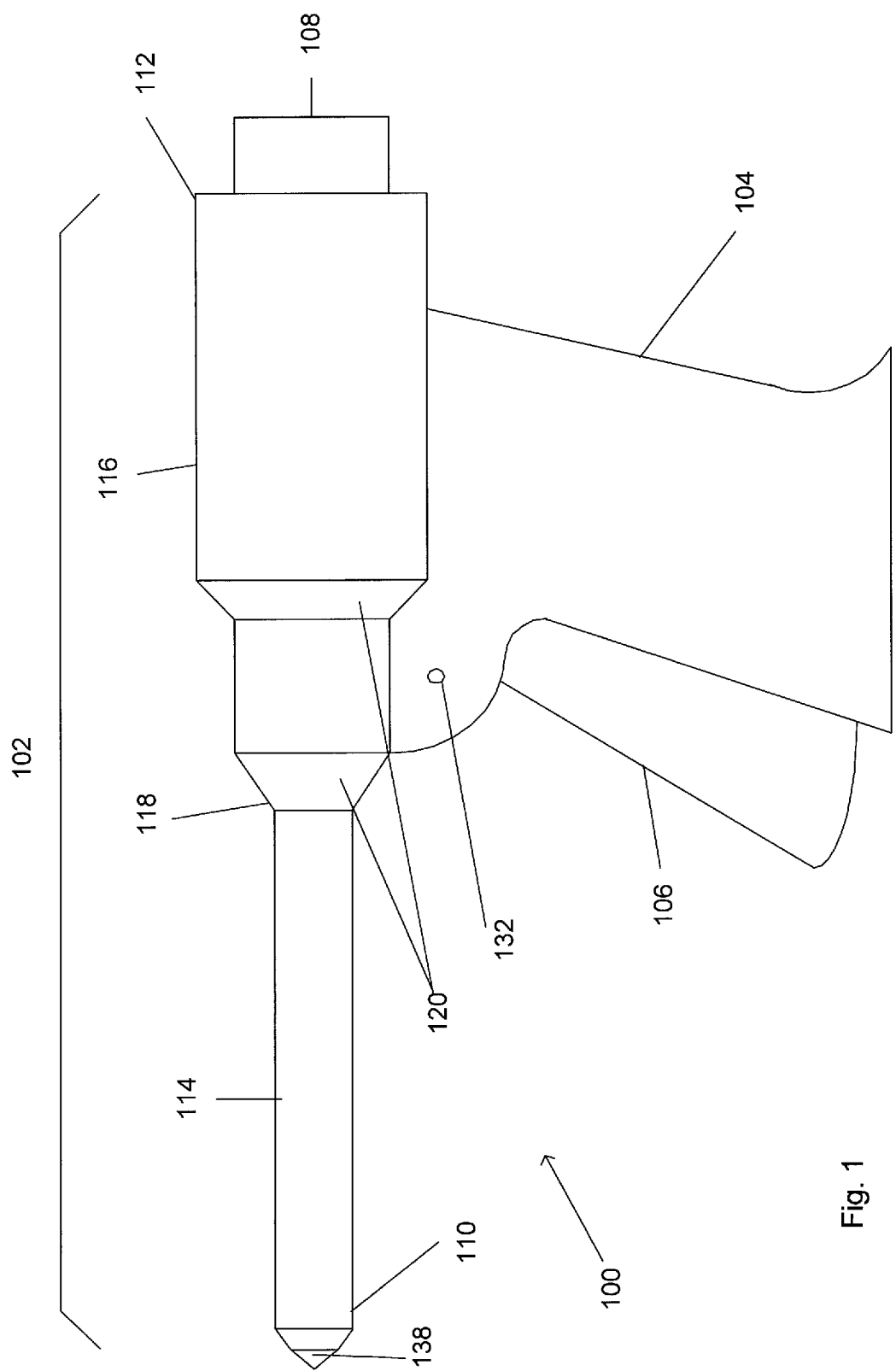
FIG. 1 shows a side view of a device according to a first embodiment of the invention in an insertion configuration.

As shown in FIGS. 1-4, a device 100 according to an embodiment of the present invention comprises a hollow body 102, a handle 104 coupled to a lever 106 and a tunneling element 108 for spreading soft tissue surrounding a bone to create room for an implant. Those skilled in the art will understand that the handle 104 may protrude laterally from the hollow body 102 or take any other shape to facilitate gripping by a user during a surgical procedure. The tunneling element 108 according to this embodiment is housed within the hollow body 102 for movement along a longitudinal axis of the device 100 when actuated by the lever 106. The hollow body 102 extends longitudinally from an open distal end 110 to an open proximal end 112 such that the tunneling element 108 may be housed within the hollow body 102 for movement along a longitudinal axis of the device 100. The hollow body 102 includes a first portion 114 which, in an operative position, is inserted through an incision into a body to a target location adjacent to a portion of bone to be accessed. A second portion 116 which remains outside the body extends proximally from a proximal end of the first portion 114. The first portion 114 is elongated and preferably has a smooth outer contour with a substantially consistent size and shape along its length. For example, if the first portion 114 is substantially tubular, its diameter will remain substantially constant along its length. The cross-sectional size of the first portion 114 (i.e., area in a plane substantially perpendicular to the longitudinal axis) is preferably selected such that the first portion 114 may fit through an incision no larger than those used for minimally invasive osteosynthesis procedures, for example, of 35 mm or less. As the second portion 116 is not inserted through the incision, it may be of a greater diameter than the distal portion 114. Those skilled in the art will understand that the term diameter as used herein is to reflect a dimension (e.g., cross-sectional area) of a particular element as it relates, for example, to the size of an incision through which the device may be inserted and is not meant to define such an element as circular or cylindrical. One or more tapered shoulders 120 may be formed along the length of the second portion 116 to make a gradual transition from the cross-sectional area of the first portion 114 to that of the second portion 116. Furthermore, those skilled in the art will understand that, as shown in FIG. 1, parts of the second portion 116 separated along the longitudinal axis (i.e., between the proximal end 112 and the distal end 118 thereof) may exhibit different cross-sectional areas as desired.

The lever 106 is movably (e.g., rotatably) coupled to the handle 104 via a peg 132 such that lever 106 may be easily pressed against the handle 104. The device 100 may further comprise a biasing member (e.g., spring 140) which returns the tunneling element 108 proximally after the lever 106 has been released. Specifically, a distal end 142 of a spring 140 abuts a shoulder 120 of the body 102 while a proximal end 144 of the spring abuts a shoulder 126 at the proximal end of the tunneling element 108.

FIG. 1 shows the device 100 in a released configuration with the lever 106 rotated clockwise through the bias of the spring 140 so that a lower end thereof is separated from the handle 104. In this position a distal end 138 of the tunneling element 108 is received within a distal end 110 of the body 102. A user may then grip the lever 106 and press it toward the handle 104, rotating the lever 106 counterclockwise as seen in FIG. 1 to move the lever 106 to an actuated position. Rotation of the lever 106 moves the tunneling element 108 distally through the lumen 115 until the distal end 138 protrudes by a desired extent from the distal end 110 of the body 102. For example, the distal end 138 may protrude between 10 and 100 mm but more preferably about 50 mm from the distal end 110. When the lever 106 is pressed against the handle 104 into the actuated configuration, the tunneling element 108 moves distally such that the shoulder 126 compresses the spring 140 and the distal end 138 of the tunneling element 108 extends distally out of the distal end 110. Thus, when pressure on the lever 106 is removed, the bias of the spring 140 urges the shoulder 126 and the tunneling element 108 proximally back into the released configuration so that the distal end 138 no longer extends distally from the distal end 110.

Figure 3:
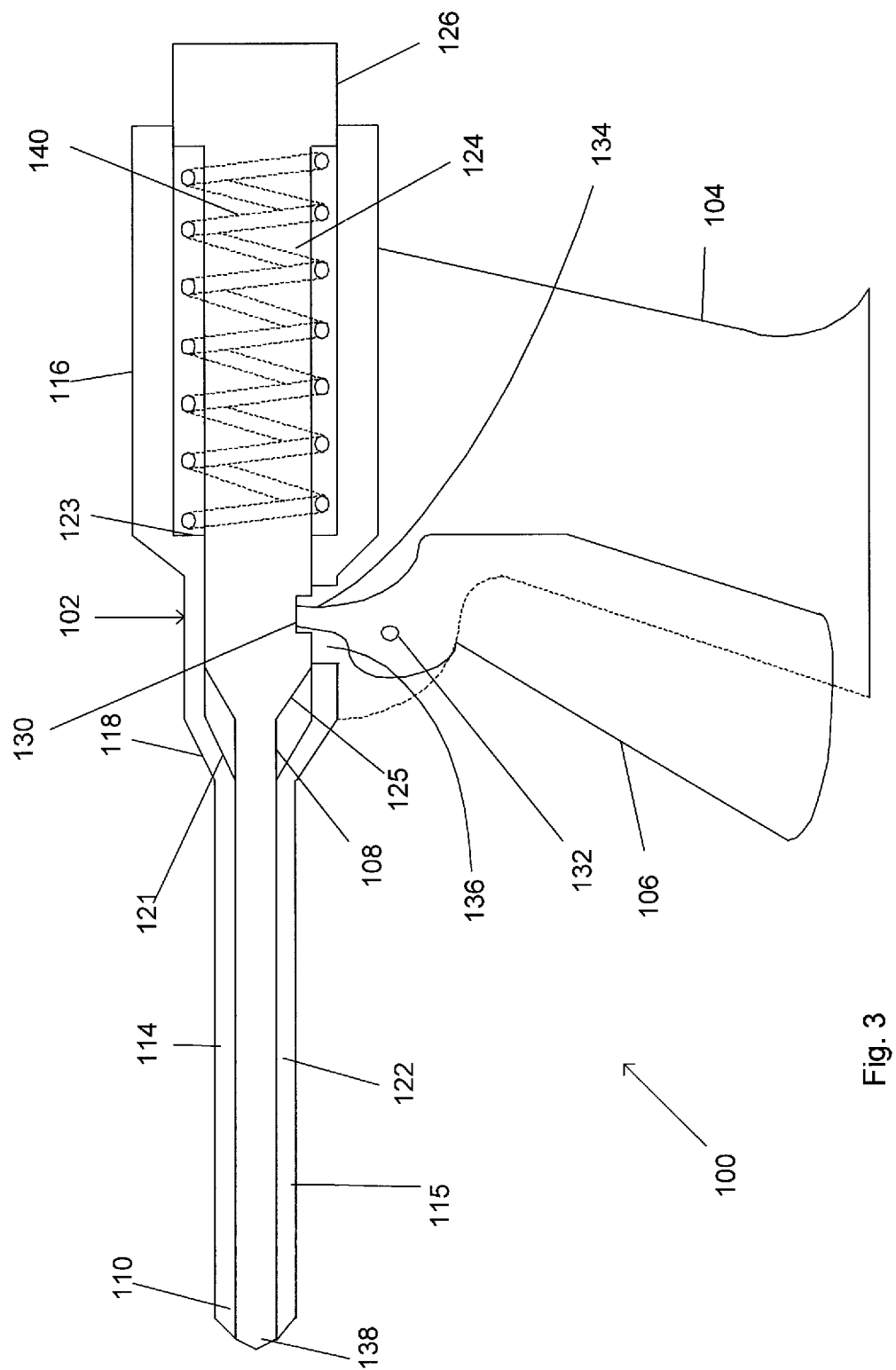
FIG. 3 shows a longitudinal cross-sectional view of the device of FIG. 1.
Figure 4:
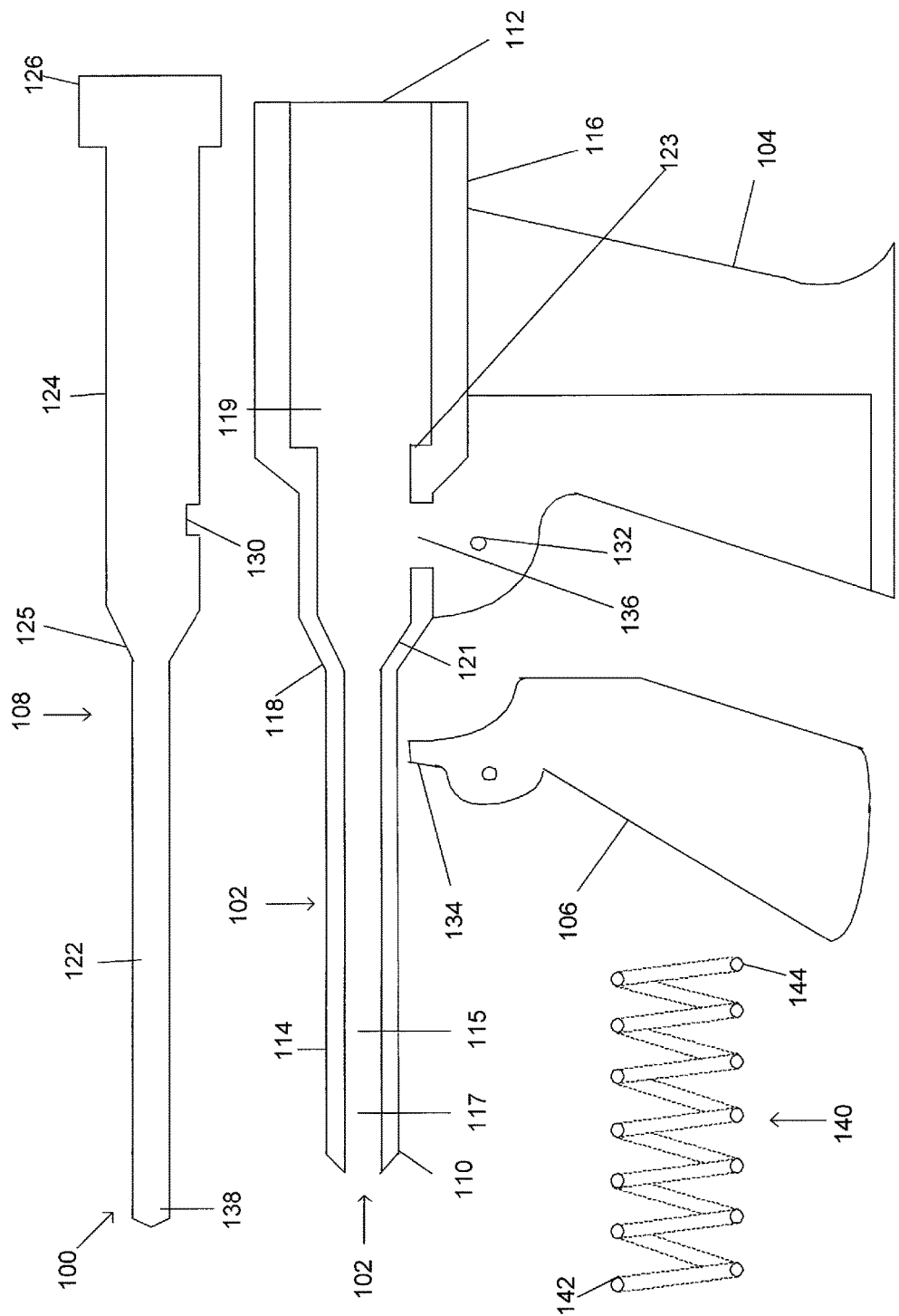
FIG. 4 shows a longitudinal cross-section view of the device of FIG. 1 disassembled.

As shown in FIGS. 3 and 4, the lumen 115 includes a distal portion 117 extending through the first portion 114 and a distal portion 119 extending through the second portion 116. The tunneling element 108 includes a first elongated portion 122 moveable within the distal portion 117 and an increased cross-sectional area second portion 124 extending proximally therefrom into the proximal portion 119 of the lumen 115. The lumen 115 may further include a necked down portion 121 gradually transitioning between the distal and proximal portions 117, 119, respectively. The first portion 122 is preferably formed as a long shaft with an outer shape and cross-sectional area sized to fit within the distal portion 117 and a tapered shoulder 125 making gradual the transition in cross-sectional area between the first and second portions 122, 124. The tunneling element 108 of this embodiment also includes a shoulder 126 formed at a proximal end thereof with a diameter of the shoulder 126 corresponding to a diameter of a portion of the lumen 115 extending proximally of a corresponding shoulder 123. A spring 140 is received in the annular space between the tunneling element 108 and the wall of this portion of the lumen 115 butting at a distal end against the shoulder 123 and at a proximal end against the shoulder 126 biasing the tunneling element 108 proximally. The user may actuate the lever 106 until a stop is reached by, for example, contact between the lever 106 and the handle 104, or between the necked down portion 121 of the lumen 115 and the tapered shoulder 125 of the tunneling element 108.

Figure 2:
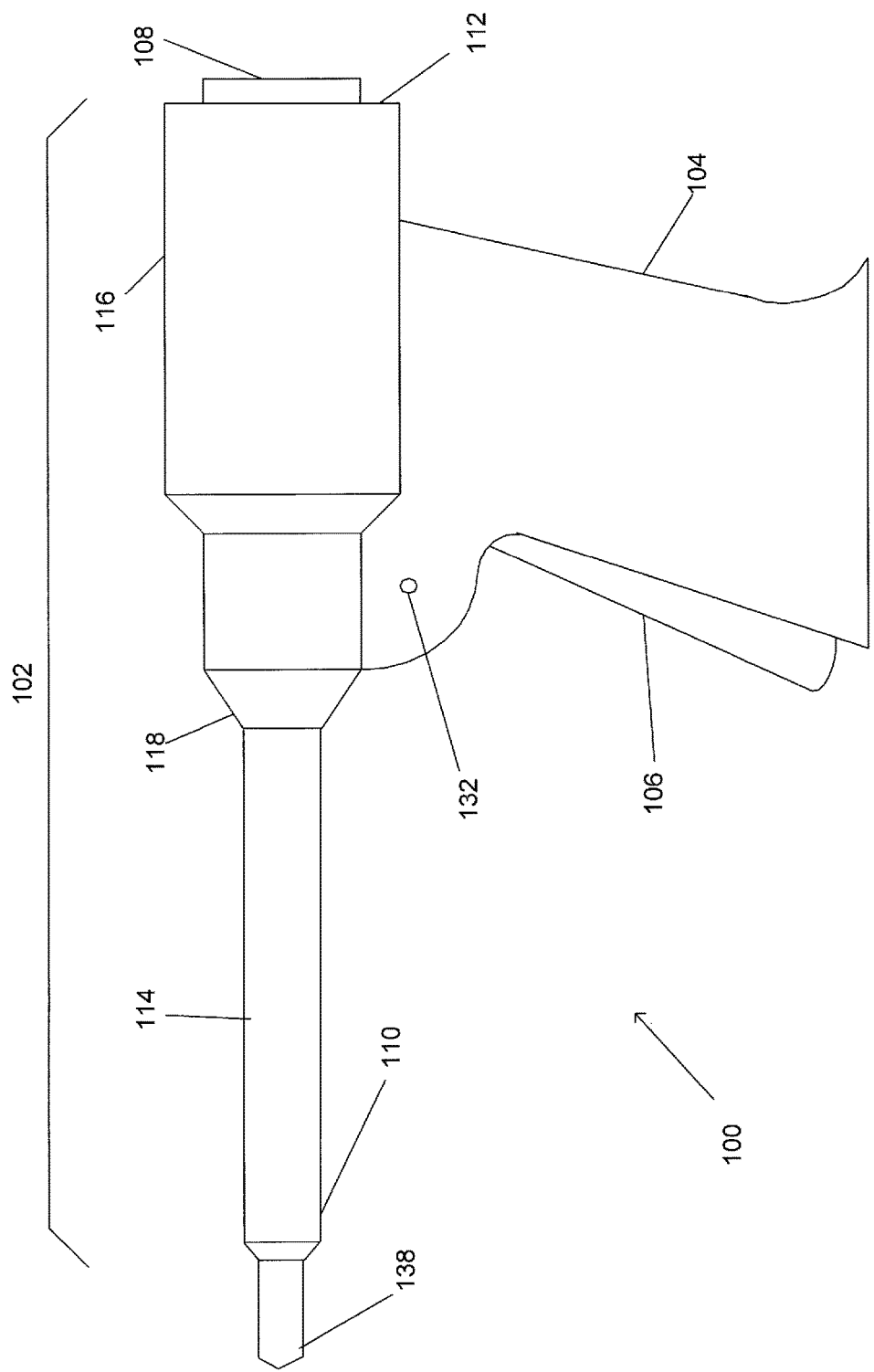
FIG. 2 shows a side view of the device of FIG. 1 in an operative configuration.

Proximal of the tapered shoulder 125 is an engaging structure (e.g., notch 130) which engages a corresponding feature of the lever 106 (e.g., a tip 134) via an opening 136 in the hollow body 102. When moved to an actuated configuration, the lever 106 is rotated about the peg 132 such that the tip 134 moves the tunneling element 108 distally through the lumen 115 moving the distal end 138 distally out of the distal end 110 of the body 102, as shown in FIG. 2. Those skilled in the art will understand that the range of motion of the tunneling agent 108 through the lumen 115 may be selected by controlling the radius about which the notch 130 rotates relative to the corresponding feature on the lever 106 and/or the range of motion of the lever 106 permitted before contact with the handle 104. Alternatively or in addition, the lumen 115 and the tunneling agent 108 may include corresponding features which engage one another to define a limit to the movement of the tunneling element 108 distally into the lumen 115. For example, the necked down portion 121 of the lumen 115 may be positioned to contact the tapered shoulder 125 when the desired maximal amount of distal movement of the tunneling element 108 has been achieved.

In an exemplary surgical technique according to the invention, a user inserts the device 100 through the skin via an incision while the device 100 is in the released configuration and advances the distal end 110 toward a target site adjacent a fractured bone to be treated. The user may advance the device 100 until a degree of resistance is felt indicating contact between the distal end 110 and soft tissues adjacent to the target site. When the distal end 110 is in the desired position relative to the target site, the user actuates the lever 106 to move the device 100 to the actuated configuration, as shown in FIG. 2, by pressing the lever 106 against the handle 104 to move the tunneling element 108 distally through the lumen 115 until the distal end 138 extends distally from the distal end 110 to gently spread the soft tissues surrounding the bone and create a tunnel for the implant. The lever 106 is then released to return the device 100 to the released configuration so that the device 100 may be repositioned (if desired) and re-actuated to increase the amount of space available for the implant. This process may be repeated as necessary. Once a sufficient amount of space has been created at the target site, the device 100 is allowed to return to the released configuration for removal from the body and the implant may be fixed to the bone in any desired manner.

Figure 5:
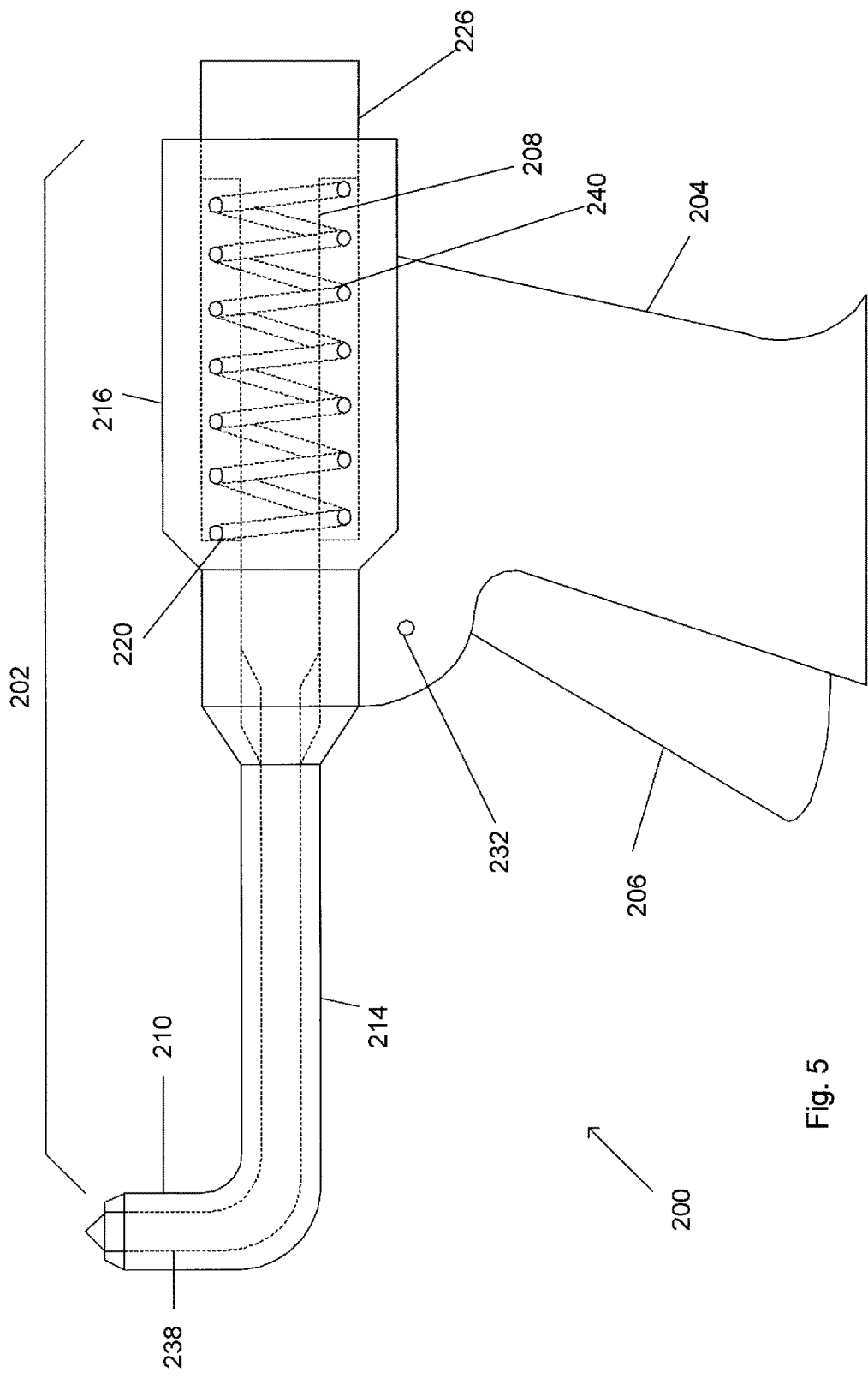
FIG. 5 shows a side view of a device according to a second embodiment of the invention.

As shown in FIG. 5, a device 200 according to a further embodiment of the invention that is substantially similar to the device 100 except that a distal end 210 of the hollow body 202 is bent in a desired curvature to facilitate the spreading of soft tissue around a circumference of a target bone. As would be understood by those skilled in the art, this may be desired when reducing a fracture using a bone cerclage tool to pass a surgical cable or wire around the bone.

As would be understood by those skilled in the art, the body 202 and the shaft 208 are preferably formed of a material to allow them to radially flex between a substantially straight insertion/retraction configuration and a curved operative configuration. The body 202 may include a first portion 214 and a second portion 216. The device 200 may include a mechanism (not shown) for moving the body 202 between the insertion/retraction configuration and the operative configuration including, for example, a pull filament coupled to the distal end 210 and extending through the body 202 to an actuator on the handle 204 so that, when pulled proximally, the filament draws the distal end 210 proximally curving the distal end 210 into the operative configuration. The distal end 210 may also be biased to revert to the insertion/retraction configuration once the tension is removed from the pull filament. The flexibility of the shaft 208 not only enables it bend between the insertion/retraction configuration and the curved operative configuration but also enables it to slide distally and proximally through the curved distal end 210 of the body 202. The shaft 208 must also retain a degree of axial stiffness sufficient to enable it to tunnel through the soft tissue surrounding the target site without deflection. Alternatively, the shaft 208 may include a flexible portion near the distal end while parts thereof which will not pass through the curved distal end 210 in the range of motion may be rigid. The rest of the construction of the device 200 may be substantially similar to that of the device 100.

In addition, a technique of use of the device 200 may also be substantially the same as that described in reference to the device 100 except that the device 200 is first placed in the substantially straight insertion configuration and inserted through an incision to the target area in the same manner described above. Then, when a target area has been reached, the device 200 is moved to the curved operative configuration using the pull filament as described above. As described above with reference to the device 100, the first portion 214 is inserted through an incision while the second portion 216 remains outside the body. The lever 206 is then pressed toward the handle 204 which is coupled thereto via a peg 232 to project the distal end 238 of the shaft 208 distally past the bent distal end 210 of the hollow body 202 to penetrate the soft tissue and create a tunnel therethrough along a path defined by the curvature of the distal end 210. Also as discussed above with reference to the device 100, the spring 240 may include a proximal end that abuts against a shoulder 220 and a distal end that abuts against a shoulder 226 of the shaft 208. As would be understood by those skilled in the art, the curved shape of the distal end 210 allows it to be moved past and around the bone to extend the tunnel to the far side of the bone. When the desired space has been created around the bone, the lever 206 is released and the bias of the spring 240 moves the shaft 208 proximally through the body 202 until the distal end 238 is retracted into the body 202. The device 200 may then be returned to the insertion/retraction configuration and withdrawn from the body.

It will be apparent to those skilled in the art that various modifications and variations can be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. A device for creating a tunnel through soft tissue, comprising:
    an elongated insertion member including a lumen extending therethrough to a distal opening, the elongated insertion member being sized to be inserted into a body via an opening of no more than 35 mm diameter, the lumen including a distal lumen section extending from the distal opening to a proximal lumen section which extends to a first shoulder, the distal lumen section having a smaller diameter than the proximal lumen section, the proximal lumen section having a smaller diameter than the first shoulder;
    a tunneling member received in the lumen for movement between an insertion configuration in which a tissue penetrating distal tip is received within the lumen and a tunneling configuration in which the distal tip extends distally from the distal opening by a desired distance, the tunneling member configured and designed to create the tunnel that is maintained after the tunneling member is removed therefrom, the tunneling member including a distal portion having a diameter corresponding to the distal lumen section, a proximal portion having a diameter corresponding to the proximal lumen section, and a second shoulder configured to engage the first shoulder to prevent the tunneling member from extending distally beyond a predetermined distance; and
    a handle coupled to a proximal end of the insertion member, the handle configured to remain outside the body and including a first actuator for moving the tunneling member between the insertion and tunneling configurations.

2. The device of claim 1, wherein the first actuator comprises a lever rotatably coupled to the handle, the lever engaging the tunneling member so that rotation of the lever relative to the handle generates a corresponding movement of the tunneling member through the lumen.

3. The device of claim 2, wherein a projection of the lever engages a notch in the tunneling member so that rotation of the lever relative to the handle in a first direction moves the tunneling member distally through the lumen and rotation of the lever relative to the handle in a second direction opposite the first direction moves the tunneling member proximally through the lumen.

4. The device of claim 1, further comprising a biasing member coupled to the tunneling member, the biasing member biasing the tunneling member to the insertion configuration.

5. The device of claim 4, wherein the biasing member comprises a spring received within the lumen around the tunneling member.

6. The device of claim 5, wherein a distal end of the spring abuts a shoulder of the lumen and a proximal end of the spring abuts a shoulder formed on a proximal end of the tunneling member.

7. The device of claim 1, wherein at least a portion of the insertion member and a portion of the tunneling member are flexible, the device further comprising a bending mechanism for moving the insertion member between the insertion configuration in which the insertion member is substantially straight and the tunneling configuration in which a distal end of the insertion member is curved.

8. The device of claim 7, wherein the bending mechanism includes a filament coupled to the distal end of the insertion member and extending through the insertion member to a second actuator on the handle.

9. The device of claim 1, wherein the lumen further includes a necked down portion between the distal and proximal lumen sections and the tunneling member further includes a tapered shoulder between the distal and proximal portions.

10. A method of treating a fracture, comprising:
    inserting through an incision to a target site adjacent to a bone to be treated, a device in an insertion configuration, the device comprising:
        an insertion member including a lumen extending therethrough to a distal opening, the elongated insertion member being sized to be inserted into a body via an opening of no more than 35 mm diameter, the lumen including a distal lumen section extending from the distal opening to a proximal lumen section which extends to a first shoulder, the distal lumen section having a smaller diameter than the proximal lumen section, the proximal lumen section having a smaller diameter than the first shoulder;
        a tunneling member received in the lumen for movement between the insertion configuration in which a tissue penetrating distal tip is received within the lumen and a tunneling configuration in which the distal tip extends distally from the distal opening by a desired distance, the tunneling member configured and designed to create the tunnel that is maintained after the tunneling member is removed therefrom, the tunneling member including a distal portion having a diameter corresponding to the distal lumen section, a proximal portion having a diameter corresponding to the proximal lumen section, and a second shoulder configured to engage the first shoulder to prevent the tunneling member from extending distally beyond a predetermined distance; and a handle coupled to a proximal end of the insertion member, the handle configured to remain outside the body and including a first actuator for moving the tunneling member between the insertion and tunneling configurations; and operating the first actuator to move the device from the insertion configuration to the tunneling configuration to create a tunnel through the tissue adjacent to the bone to be treated.

11. The method of claim 10, further comprising returning the device to the insertion configuration and withdrawing the device from the body.

12. The method of claim 10, further comprising releasing the first actuator to allow a biasing member to move the device from the tunneling configuration to the insertion configuration.

13. The method of claim 10, wherein the insertion member is maintained substantially straight during insertion and a desired curve is formed in the distal end thereof after the distal end has reached a desired position adjacent to the target site.

14. The method of claim 13, further comprising positioning the curved distal end of the insertion member around the bone to be treated so that, when moved to the tunneling configuration, a tunnel is created in tissue around the bone.

15. The method of claim 10, further comprising positioning n distal end of the insertion member alongside a bone to be treated so that the distal tip spreads tissue alongside the bone when the device is moved to the tunneling configuration.

16. The method of claim 11, further comprising, after returning the device to the insertion configuration, moving the insertion member to another target site and returning the device to the tunneling configuration to enlarge the tunnel through the tissue adjacent to the bone to be treated.

17. The method of claim 10, wherein the lumen further includes a necked down portion between the distal and proximal lumen sections and the tunneling member further includes a tapered shoulder between the distal and proximal portions.

* * * * *

UNITED STATES PATENT AND TRADEMARK OFFICE
CERTIFICATE OF CORRECTION

PATENT NO. : 10,524,816 B2
APPLICATION NO. : 12/515817
DATED : January 7, 2020
INVENTOR(S) : Dell'Oca Page 1 of 1

It is certified that error appears in the above-identified patent and that said Letters Patent is hereby corrected as shown below:

In the Claims

Claim 15, Column 8, Lines 10-11:
"15. The method of claim 10, further comprising positioning n distal end of the insertion member alongside a bone to"
Should read:
"15. The method of claim 10, further comprising positioning a distal end of the insertion member alongside a bone to"

Signed and Sealed this
Twentieth Day of July, 2021

Drew Hirshfeld
*Performing the Functions and Duties of the
Under Secretary of Commerce for Intellectual Property and
Director of the United States Patent and Trademark Office*